US009817002B2

(12) United States Patent
Dasgupta et al.

(10) Patent No.: US 9,817,002 B2
(45) Date of Patent: Nov. 14, 2017

(54) MOLECULAR DISCRIMINATORS USING CARBON NANOTUBES

(75) Inventors: Anjan Kr. Dasgupta, Kolkata (IN); Tamoghna Bhattacharyya, Dist-Birbhum (IN)

(73) Assignee: UNIVERSITY OF CALCUTTA, Kolkata (IN)

( * ) Notice: Subject to any disclaimer, the term of this patent is extended or adjusted under 35 U.S.C. 154(b) by 325 days.

(21) Appl. No.: 14/403,124

(22) PCT Filed: Aug. 6, 2012

(86) PCT No.: PCT/IB2012/001509
§ 371 (c)(1),
(2), (4) Date: Mar. 13, 2015

(87) PCT Pub. No.: WO2013/175259
PCT Pub. Date: Nov. 28, 2013

(65) Prior Publication Data
US 2015/0185237 A1 Jul. 2, 2015

(30) Foreign Application Priority Data
May 23, 2012 (IN) .............................. 592/KOL/2012

(51) Int. Cl.
*G01N 33/92* (2006.01)
*B01J 19/00* (2006.01)
*B82Y 30/00* (2011.01)
*G01N 21/65* (2006.01)
*G01N 21/64* (2006.01)
*G01N 21/35* (2014.01)

(52) U.S. Cl.
CPC .............. *G01N 33/92* (2013.01); *B82Y 30/00* (2013.01); *G01N 21/6408* (2013.01); *G01N 21/6458* (2013.01); *G01N 21/65* (2013.01); *G01N 2021/3595* (2013.01)

(58) Field of Classification Search
CPC ........ G01N 31/00; G01N 33/92; G01N 33/50; G01N 33/48; B01J 19/0006; B01J 19/0046; B01J 19/00
USPC ......................................................... 436/34
See application file for complete search history.

(56) References Cited

U.S. PATENT DOCUMENTS

| 2004/0018543 A1* | 1/2004 | Balavoine | B82Y 30/00 435/6.19 |
|---|---|---|---|
| 2007/0114138 A1 | 5/2007 | Krasteva et al. | |
| 2009/0166523 A1 | 7/2009 | Bachmann et al. | |
| 2009/0166560 A1 | 7/2009 | Dai et al. | |
| 2010/0025330 A1 | 2/2010 | Ratto et al. | |
| 2010/0086933 A1 | 4/2010 | Hospach et al. | |
| 2010/0227913 A1* | 9/2010 | Lyakhov | C12Q 1/6818 514/44 R |

FOREIGN PATENT DOCUMENTS

CN 101294926 A 10/2008

OTHER PUBLICATIONS

Merriam Webster definition of 'interference.' Merriam-Webster.com, obtained on Apr. 6, 2017, pp. 1-8.*
Shim, M. et al., "Functionalization of Carbon Nanotubes for Biocompatibility and Biomolecular Recognition," Nano Letters, 2002, 2 (4), pp. 285-288.
Bhattacharyya, T., et al., "Molecular discriminators using single wall carbon nanotubes," Nanotechnology, Sep. 4, 2012, vol. 23, No. 38, pp. 1-8.
Colomer, J.F., et al., "Large-scale synthesis of single-wall carbon nanotubes by catalytic chemical vapor deposition CCVD method," Chemical Physics Letters, vol. 317, Jan. 28, 2000, pp. 83-89.
Dayani, Y., and Malmstadt, N., "Formation of covalently anchored lipid bilayers on multi-walled carbon nanotubes," USC Viterbi School of Engineering, accessed on Oct. 31, 2014, pp. 1-2.
Girifalco, L. A., et al., "Carbon nanotubes, buckyballs, ropes, and a universal graphitic potential," Physical Review B, Nov. 15, 2000, vol. 62, No. 19, pp. 13104-13110.
International Search Report and Written Opinion for counterpart International Patent Application No. PCT/IB2012/001509 dated Feb. 8, 2013.
Lee, J. Y., et al., "Modeling the Self-Assembly of Copolymer-Nanoparticle Mixtures Confined between Solid Surfaces," Phys. Rev. Lett., Sep. 26, 2003, vol. 91, No. 13, pp. 136103-1 to 136103-4.
Lu, Y., et al., "Self-assembly of mesoscopically ordered chromatic polydiacetylene/silica nanocomposites," Nature, vol. 410, pp. 913-917 (2001).
Moskovits, M., "Surface-enhanced spectroscopy," Rev. Mod. Phys, J, vol. 57, No. 3, pp. 1-46 (Jul. 1985).
Moustafa, M. A., et al., "Kinetics of Solid State Reactions Co2, Cu2 and Zn2 Basic Carbonates with Some Aliphatic Acids," Journal of Thermal Analysis and Calorimetry, vol. 63, No. 2, pp. 609-618 (2000).
Qureshi, M., et al., "Kinetics and mechanism of p-dimethylaminobenzaldehydediphenylamine hydrochloride reaction in the solid state," J. Phy. Chem, vol. 79, No. 2, pp. 116-118 (1975).
Rastogi, R. P., and Singh, N.B., "Solid-State Reactions between Picric Acid and Naphthols," J. Phys. Chem, vol. 70, No. 10, pp. 3315-3324 (1966).
Rastogi, R. P., et al., "Kinetics of Reaction Between Naphthalene and Picric Acid in the Solid State," J. Phys. Chem, vol. 66, No. 12, pp. 2707-2708, (1962).

(Continued)

*Primary Examiner* — Christine T Mui
(74) *Attorney, Agent, or Firm* — Maschoff Brennan

(57) ABSTRACT

Methods including contacting, in the solid state, a sample comprising a first organic molecule with a composition comprising: a carbon nanotube, such that an interface forms between the sample and the composition; observing any movement of the interface; and characterizing the first organic molecule based on the observed movement are described.

21 Claims, 15 Drawing Sheets

(56) References Cited

OTHER PUBLICATIONS

Rastogi, R. P., et al., "Mechanism of the Reaction Between Hydrocarbons and Picric Acid in the Solid State," J. Phys. Chem, vol. 67, No. 12, pp. 2569-2573 (1963).

Thess, A., et al., "Crystalline Ropes of Metallic Carbon Nanotubes" Science, vol. 273, No. 5274, Jul. 26, 1996, pp. 483-487.

Wang, Y., and Zerda, T. W., "The mechanism of the solid-state reaction between carbon nanotubes and crystalline silicon under high pressure and at high temperature," J. Phys.: Condens. Matter, vol. 18, No. 11, pp. 2995-3003 (2006).

Zull, J. E., et al., "Interaction of Egg Lecithin with Cholesterol in the Solid State," Biochemistry, vol. 7, No. 12, 4172-4176 (1968).

* cited by examiner (c)

(b)

(a)

(c)

(b)

(a)

(b)

(a) t=0min
(b) t=40 min (a) t=0 min
(b) t=40 min

MOLECULAR DISCRIMINATORS USING CARBON NANOTUBES

CROSS-REFERENCE TO RELATED APPLICATIONS

This application is a U.S. National Phase application under 35 U.S.C. §371 of International Application No. PCT/IB2012/001509, filed on Aug. 6, 2012, which claims priority to Indian Application No. 592/KOL/2012, filed on May 23, 2012, the entire content of each of which is incorporated herein by reference in its entirety for any and all purposes.

BACKGROUND

The following description is provided to assist the understanding of the reader. None of the information provided or references cited is admitted to be prior art.

Carbon nanotubes (CNTs) have increasingly been used as chemical sensors and probes. Such uses often require dispersions of CNTs in a liquid or solid host medium. However, creating such dispersions of CNTs in the host medium has been a major challenge. For example, CNTs tend to agglomerate and bundle together causing many site defects in a CNT composite. Functionalization of the CNT is one method to prevent agglomeration and improves the compatibility of CNT and the host material.

The functionalization process is not without drawbacks: it is often slow, difficult, and uses harmful chemicals. For example, CNT may be functionalized with an amino group. This functionalization, however, may lead to alteration of the desired properties of the CNT (e.g., its hydrophobic character, chirality, effective length, cross sectional area of the CNT, etc.). Additionally, for single wall carbon nanotubes (SWNTs), functionalization may lead to the formation of undesirable cross-linked structures, which may ultimately change the native signature characteristic of this unique nanostructure.

Unless functionalized, CNTs, such as SWNTs, are hydrophobic. As a result, CNTs often have difficulty interacting with certain molecules, such as amphiphilic molecules (e.g., amphiphilic lipids, detergents, etc). In particular, when these amphiphilic molecules are in an aqueous state, they tend to take on complex vesicular or micelle forms, that encapsulate the hydrophobic CNT, and prevent formation of an interface in which the CNTs directly interact with the entire structures of amphiphilic molecules. Thus, many challenges remain with respect to using CNTs as chemical sensors and probes.

SUMMARY

Provided in one aspect is a method, including: contacting, in the solid state, a sample including a first organic molecule with a composition including a carbon nanotube, such that an interface forms between the sample and the composition; observing any movement of the interface; and characterizing the first organic molecule based on the observed movement.

Provided in another aspect is a method, the method including contacting, in the solid state, a sample including at least one of (i) an amphiphilic organic molecule and (ii) a non-amphiphilic organic molecule with a composition including a carbon nanotube, such that an interface forms between the sample and the composition; observing any movement of the interface; and characterizing the carbon nanotube based on the observed movement.

Provided in another aspect is a method of functionalizing a composition including a carbon nanotube; the method including: contacting, in the solid state, a first organic molecule including a hydrophobic group with a composition including a carbon nanotube, such that at least a portion of the carbon nanotube is reoriented upon contact with the first organic molecule.

The foregoing summary is illustrative only and is not intended to be in any way limiting. In addition to the illustrative aspects, embodiments and features described above, further aspects, embodiments and features will become apparent by reference to the following drawings and the detailed description.

DETAILED DESCRIPTION

Figure 1:
FIG. 1 provides a schematic representation of solid state capillary reaction in an illustrative embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented here.

The technology is described herein using several definitions, as set forth throughout the specification.

The use of the terms "a" and "an" and "the" and similar referents in the context of describing the elements (especially in the context of the following claims) are to be construed to cover both the singular and the plural, unless otherwise indicated herein or clearly contradicted by context.

As used herein, "about" will be understood by persons of ordinary skill in the art and will vary to some extent depending upon the context in which it is used. If there are uses of the terms which are not clear to persons of ordinary skill in the art, given the context in which it is used, "about" will mean up to plus or minus 10% of the particular term—e.g., ±7%, ±5%, ±4%, ±3%, ±2%, ±1%, ±0.5%, ±0.2%, ±0.1%, or ±0.05%.

As used herein, "substantially free" will be understood by persons of ordinary skill in the art to mean completely or almost completely free of something. Thus, e.g., "substantially free of fluorescence" means completely or almost completely free of fluorescence. Examples of "substantially free" of something include exhibiting or containing less than or equal to 90%, less than or equal to 91%, less than or equal to 92%, less than or equal to 93%, less than or equal to 94%, less than or equal to 95%, less than or equal to 96%, less than or equal to 97%, less than or equal to 98%, or less than or equal to 99% of something such as fluorescence.

In one aspect, a method to characterize a molecule is provided, the method including contacting, in the solid state, a sample including a first organic molecule with a composition including a carbon nanotube, such that an interface forms between the sample and the composition; observing any movement of the interface; and characterizing the first organic molecule based on the observed movement.

Carbon nanotubes (CNTs) may be a subset of the nanotubes; CNTs may refer to a nanotube including carbon atoms, such as consisting essentially of carbon atoms, such as consisting of carbon atoms. Carbon nanotubes, in general may have a long hollow structure with the walls formed by one-atom-thick sheets of carbon atoms. These sheets may be rolled at specific and discrete ("chiral") angles, and the combination of the rolling angle and radius may determine the nanotube properties. Carbon nanotubes may be categorized as single-walled nanotubes (SWNTs) and multi-walled nanotubes (MWNTs). Individual nanotubes may align themselves into "ropes" held together by van der Waals forces, more specifically, pi-stacking. In some instances herein, CNTs may refer to nanotube comprising graphene—e.g., a graphene sheet rolled into a tubular structure. More generally, CNTs herein may refer to allotropes of carbon with generally a cylindrical nanostructure.

The structure need not be entirely cylindrical and may be a geometry that is similar to a tubular structure. In general, a CNT may have a high aspect ratio (length-to-diameter), which in many instances is higher than other materials. For example, the ratio may be at least about 10—e.g., at least about 100, at least about 1000, at least about 10,000, at least about 100,000, at least about 1000,000, at least about 10,000,000, at least about 100,000,000, or more. The CNTs described herein may have any dimensions. For example, the CNTs may have a diameter of about 1 to about 10 nm, e.g., about 1 nm, about 2 nm, about 3 nm, about 4 nm, about 5 nm, about 6 nm, about 7 nm, about 8 nm, about 9 nm, about 10 nm or any range between and/or including two or more such values.

The first organic molecule referred herein may be any organic molecule suitable for the various applications for which the methods and systems described herein may be employed. For example, the organic molecule may be an amphiphilic molecule, such a detergent. An amphiphilic molecule is a molecule that exhibits both hydrophilic and lipophilic properties. In other words, an amphiphilic molecule may have hydrophobic and polar regions, either or both of which can be used as an interacting probe. As will be discussed below, in some embodiments, different amphiphilic molecules may exhibit different diffusion behavior as they interact with the same carbon nanotube; on the other hand, different carbon nanotubes may also exhibit different diffusion behaviour as they interact with the same amphiphilic molecule.

In some embodiments, the organic molecule may comprise (or be) a lipid. Lipids include hydrophobic regions or moieties but may also be amphiphilic and include a polar region or moiety. Thus lipids include but are not limited to fatty acids, glycerolipids (e.g., mono-, di- and tri-glycerides), phospholipids, glycolipids, sphingolipids (e.g., sphingosine, sphingomyelins, and the like), or a combination of any two or more thereof. In some embodiments, the organic molecule is a phospholipid or may include a phospholipid moiety. For example, the organic molecule may be at least one of lecithin, dipalmitoyl phosphatidylcholine (DPPC), or a sphingomyelin. The lipid may be, for example, an omega-3 fatty acid. An omega-3 fatty acid may be, for example, linolenic, linoleic acids, and the like. Depending on the type of organic molecule (e.g., lipid), different types of CNTs may be used. For example, in one embodiment wherein the organic molecule is a steroid (e.g., cholesterol), the nanotubes employed may be one including graphene.

The lipid described herein may have various types of chemical structures. For example, the lipid may have a linear, unbranched, hydrophobic group (or moiety), a branched hydrophobic group, or a combination of both. In some embodiments, the lipid may include a saturated, unsaturated, or both, $C_4$-$C_{30}$ hydrocarbon group. For example, the hydrocarbon group may be an alkyl group, an alkenyl group, an alkynyl group, an aryl group or an aralkyl group. In some embodiments the hydrocarbon group may have 4, 6, 8, 10, 12, 14, 16, 18, 20, 22, 24 or 30 carbons or a range between and/or including any two such values.

In one aspect of the present methods, the CNTs may function as a molecular probe to observe and/or characterize an organic molecule(s) in the sample, such as any of the organic molecules described above, in the solid state. The CNTs may be a part of a composition. The probe may be used to observe, and thus characterize, the organic molecule via the interaction between the two.

In some embodiments, a composition including CNTs, such as hydrophobic CNTs, is allowed to interact with different hydrophobic, amphiphilic, or non-amphiphilic molecules in a narrow capillary interface. These molecules may be any of the organic molecules described herein. Although the CNTs may be functionalized, one surprising advantage of the methods and systems described herein is that the CNTs need not be functionalized (prior to the observation) to serve and act as a molecular probe. In other words, the presently described systems and methods do not need surfactants, heating, or harmful chemicals (as do most functionalization processes via chemical routes conventionally applied in the art).

In an illustrative embodiment, the sample includes a lipid with both a hydrophobic moiety and a polar moiety, and the contact at the interface between the lipid and the hydrophobic CNTs may lead to a re-structuring of the lipid moieties at regions close to the interface. In some embodiments, the systems and the methods described herein used the observation of the re-restructuring as a mechanism to characterize or identify the interaction between the CNTs and the lipid organic molecule.

The CNT composition and the organic molecule may be brought into contact at any suitable conditions, depending on the materials involved. For example, the contacting process may be carried out at ambient conditions—e.g., room temperature, 1 atm., etc. Other conditions may also be employed. The contacting process may be carried out at the aforedescribed conditions, or any other conditions, depending on the molecules. For example, the contacting may be carried out for between about 2 hours and about 10 hours—e.g., about 2 hours, about 3 hours, about 4 hours, about 5 hours, about 6 hours, about 7 hours, about 8 hours, about 9 hours or a range between and including any two such time periods. Longer or shorter time durations may also be employed.

As described herein, the organic molecule(s) may be characterized by observing the interaction between the molecule(s) and the CNT (probe). For example, the characterization may be based on the movement of the organic molecule during the contact (e.g., as a result of the re-structuring of the molecule due to the contact). The re-structuring may include reorientation of the organic molecules due to the contact. Alternatively, the CNTs may also exhibit reconfiguration of their structure. In some embodiments, a portion of the carbon nanotube may be reoriented upon contact with the first organic molecule.

In some embodiments, the interaction causes formation of an interface between the sample (organic molecules) and the CNTs. Thus, the interface between the molecule and the CNTs may be monitored (by the techniques described below). In some embodiments, the interface may exhibit quantum confinement. In some embodiments, as a result of the contact, the CNTs may become non-covalently functionalized at the interface with the first organic molecule.

In some embodiments, the CNTs (and thus the composition comprising the CNTs) may diffuse towards the sample and the geometry of the interface and the rate and/or the extent of diffusion movement of the interface (between the molecule and the CNTs) is dependent on the lipid structure. In other embodiments, the CNTs may diffuse towards the organic molecules; and similar to the diffusion process of the organic molecules towards CNTs, the diffusion of CNT may be affected by the geometry of the interface and the rate and/or the extent of diffusion movement of the interface. In some other embodiment, diffusion in both directions may occur. Thus, any of these changes may serve as an indicator to characterize the particular organic molecules (e.g., lipids) being observed.

The observation may be carried out by a variety of techniques, depending at least on the types of the organic molecules and the properties of interest. For example, the observation may be carried out via optical microscopy, fluorescence microscopy, Raman microscopy, infra-red imaging, thermal imaging, or a combination of any two or more thereof.

Fluorescent microscopy may be used as one example to observe the interface. Any suitable fluorescent microscopy techniques, including various settings depending on the materials and instruments involved, may be employed. In some embodiments, the fluorescence spectra of the interface between carbon nanotubes and a lipid may taken by assembling fluorescence microscopy with fluorescence spectroscopy (PTI). The excitation wavelength may be between about 200 nm and about 500 nm—e.g., between about 250 nm and 450 nm, or between about 300 nm and 400 nm. In one embodiment, the excitation wavelength may be about 360 nm and emission may be observed at about 450 nm in fluorescence spectroscopy.

In some embodiments, fluorescent microscopy may reveal a sharp fluorescent layer at the interface and the fluorescence intensity may be dependent on the diffusion movement of the molecule. This technique is useful in several instances because fluorescence is observed at the interface, but the first organic molecule and the composition not at the interface are substantially free of fluorescence—thereby providing a good contrast at the interface. Although not wishing to be bound by theory, it is nevertheless believed that the luminescence emission at the interface is generally brighter due to the passivation of nanotubes surface upon functionalization: when electrons and holes (i.e., exciton pairs) generated by photons are confined within a space, or quantum box, that is smaller than the Bohr exciton radius, the semiconductor's band gap widens and its fluorescence shifts towards the blue. Quantum confinement of both the electron and hole may lead to an increase in the effective band gap of the material upon functionalization. As a result, the emission of quantum mechanically confined material shifts to the blue spectrum (i.e., higher energy). In general, the intensity is higher when the size of the quantum box gets smaller. In some embodiments, the fluorescence intensity is higher for more ordered, polarized materials in nano-dimension, as compared to a geometry that is less ordered and/or fractal. Accordingly, in one embodiment, the fluorescence intensity of lecithin functionalized SWNT (ordered, polarized functionalized material) may be higher than that of DPPC functionalized SWNT (less ordered, fractal functionalized material).

The degree of diffusion may be different for the different lipids, and thus the type of lipid and other properties associated therewith may be identified and/or characterized by observing the diffusion phenomena of the lipid (with respect to the CNT probe). For example, a single tail (or linear) lipid (e.g., lecithin) may exhibit a higher extent of diffusion drift as compared to a branched lipid (e.g. dipalmitoyl phosphatidylcholine, or DPPC). Additionally, for the same lipid (e.g. lecithin) SWNT and MWNT may show different reaction diffusion patterns, and thus the differences in the probes used may also need to be accounted for.

As a result, the methods and probe systems described may provide a mechanism to identify an organic molecule by observing the molecule's diffusion (e.g., by changes in fluorescence and/or geometry) with respect to the probe. Further, the methods and probe systems described herein may be used to distinguish one molecule from another based on their respective interactions with the probe. In some embodiments, the aforedescribed processes may be repeated for at least a second (or more) molecule(s), and the first molecule and the second molecule may be distinguished based on their respective interactions (i.e., the phenomena taking place at the respective interfaces).

Additionally, the methods described herein provide a simple solid-state "single pot" process of functionalizing a CNT with different molecules without chemical pre-processing. The methods described herein may need only a simple set-up—e.g., using only the CNTs and the molecules (e.g., lipids or whatever molecule that is used) and can be performed at standard temperature and pressure, such as ambient conditions.

EXAMPLES

Materials and Chemicals

The following materials and chemicals were used in the Examples below. Highly purified single wall carbon nanotubes (SWNT), highly purified multiwall carbon nanotubes (MWNT), L-alpha phosphatidylcholine (lecithin) from Sigma Aldrich, dipalmitoyl phosphatidylcholine (DPPC) from Sigma Aldrich, and other equipment (e.g., glass capillary tubes, glass slides, needles, etc.) were used to for the study described in this Example.

Example 1: Capillary Technique

The kinetics of solid state reaction was studied in capillary tubes. SWNT and MWNT were synthesized by a catalytic chemical vapor deposition method; an example of which may be found in Colomer et al., Large-scale synthesis of single-wall carbon nanotubes by catalytic chemical vapor deposition (CCVD) method Chem. Phys. Lett. 317 83-89 (2000).

One end of the capillary was sealed with lipids and CNTs were tightly stacked from the other end as very negligible reactions occur between two reactants if there is a spacing of known distance between two materials. The capillary tubes were fixed on glass slides for microscopic measurements at room temperature. The kinetics of the reaction was followed by observing the migration of the interface meniscus with the help of a microscope (Nikon Eclipse Ti-U).

As shown in FIG. 1, X and Y are two nano-materials, B being the interface of separation. The interface will diffuse only if the reaction occurs and one expects a molecular reorientation at the interface. Such reorientation, if any, can be considered as a nano-scale reaction that would be coupled to a diffusive or translocation mechanism, as in a solid state chemical reaction.

Example 2: Fluorescence Study

The fluorescence images (blue fluorescence) were captured in a regular interval of time by normal fluorescence microscopy (Nikon Eclipse Ti-U) upon UV excitation. The fluorescence spectra of SWNT-lipids interface region were taken by assembling fluorescence microscopy with fluorescence spectroscopy (PTI). The excitation wavelength was 360 nm and emission was observed at ~450 nm in fluorescence spectroscopy.

The kinetics study was also performed upon excitation of the samples by three different fluorescent lights (UV, Blue, and Green) in the lipid part, CNT part, and the interface region; and the emission spectrum pattern was observed in these aforedescribed three regions at a regular time interval. The fluorescence spectra of SWNT-lipid interface region was captured in solid state, keeping the capillary fixed at the microscope bench; and the method for capturing the fluorescence spectra in solid state was developed.

Example 3: Fourier Transform Infra Red (FT-IR) Imaging

The imaging study was monitored by a FT-IR Microscope (JASCO FT/IR-6300), with equipment settings as already provided above. Experiments were carried out in capillary condition, which was designed on a plate and kept fixed at microscope bench at room temperature. The capillary set-up involved glass cover slips (i.e. glass cover slips were cut and assembled to make a capillary), and the experiment was continued in inert atmosphere and the images were captured keeping the detector in reflectance mode. The whole imaging experiment was continued in liquid nitrogen environment because it is recommended to keep the reflectance and transmission detector in cool condition. A small area covering the interface, CNT part, and lipid part was selected for this study. Infrared light scans every pixel of that selected region and gives the total IR images and spectra of that region. The entire experiment was continued for about 5 to 6 hours, and the IR images were captured in a regular time interval. The pool of imaging data provided total information on diffusion pattern of the interface region.

Results and Discussions

Microscopic Bright Field Images

Figure 2:
FIGS. 2(a)-2(c) show a series of microscope bright field images of SWNT-lecithin interface at different time intervals in an illustrative embodiment; 2(b) and 2(c) were taken 30 minutes and 50 minutes, respectively, after the first image was taken.
Figure 2:
Figure 2:
Figure 7:
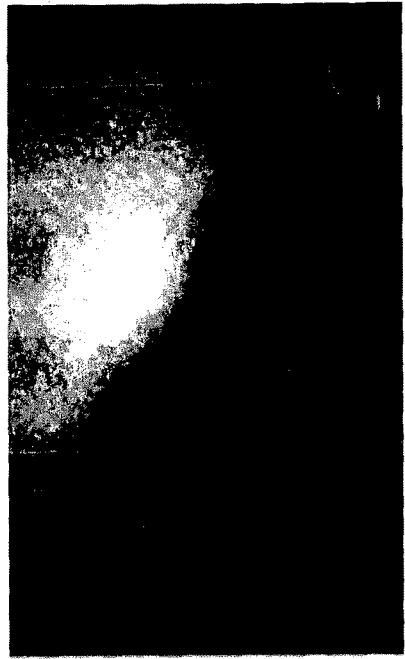
FIGS. 7(a)-7(b) show bright field images of MWNT-lecithin interfaces in an illustrative embodiment.
Figure 7:

The migration of the SWNT-lipid and MWNT-lipid meniscus was observed by taking snapshots of photographs at a regular time interval via a microscope (normal Nikon Eclipse Ti-U fluorescence microscope, as described above). The result is shown in FIGS. 2 and 7—the left hand side is the SWNT/MWNT part and the right most side is the lipid part as shown in FIGS. 2(a)-2(c) and FIGS. 7(a)-7(b) respectively. The curvature denotes the interface region of SWNT/MWNT and lipid. The interface meniscus diffuses to the lipid moiety with a very slow rate. The experiments were repeated for 5 to 6 times; and same results were obtained.

It was also observed that the diffusion rate of the meniscus was positive in the first few cases, but after few hours the curvature of the meniscus does not change with time, i.e. it remains fixed. Mathematically if 'A' is the distance of the perimeter of the diffusing interface from the previous interface, then initially $(dA/dt)>0$, but a few hours later $(dA/dt)=0$, wherein t represents time.

Fluorescence Study

The diffusion study was also observed by fluorescence microscopy. When the capillary was excited in UV-radiation only, a sharp fluorescent layer in the interface was observed, but the emission characteristics were not found either in CNT side or lipid side. In other words, the fluorescence was observed only at the interface, as shown by a sharp blue fluorescence observed in the interface of CNT-lipid interfaces.

Figure 3:
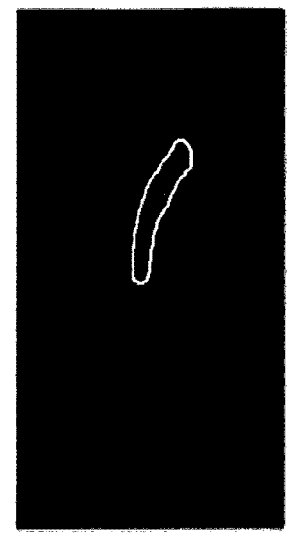
FIGS. 3(a)-3(c) show a series of fluorescent images of SWNT-lecithin interface at different time intervals in an illustrative embodiment; 3(b) and 3(c) were taken 30 minutes and 50 minutes, respectively, after the first image was taken.
Figure 3:
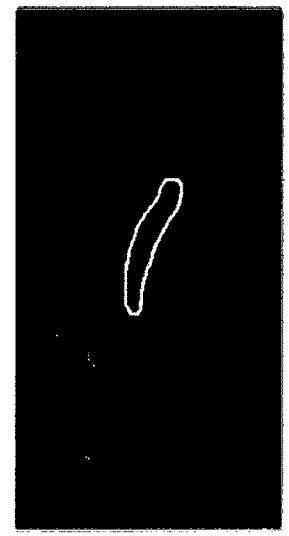
Figure 3:
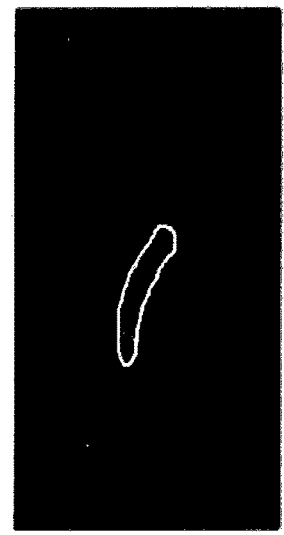
Figure 4:
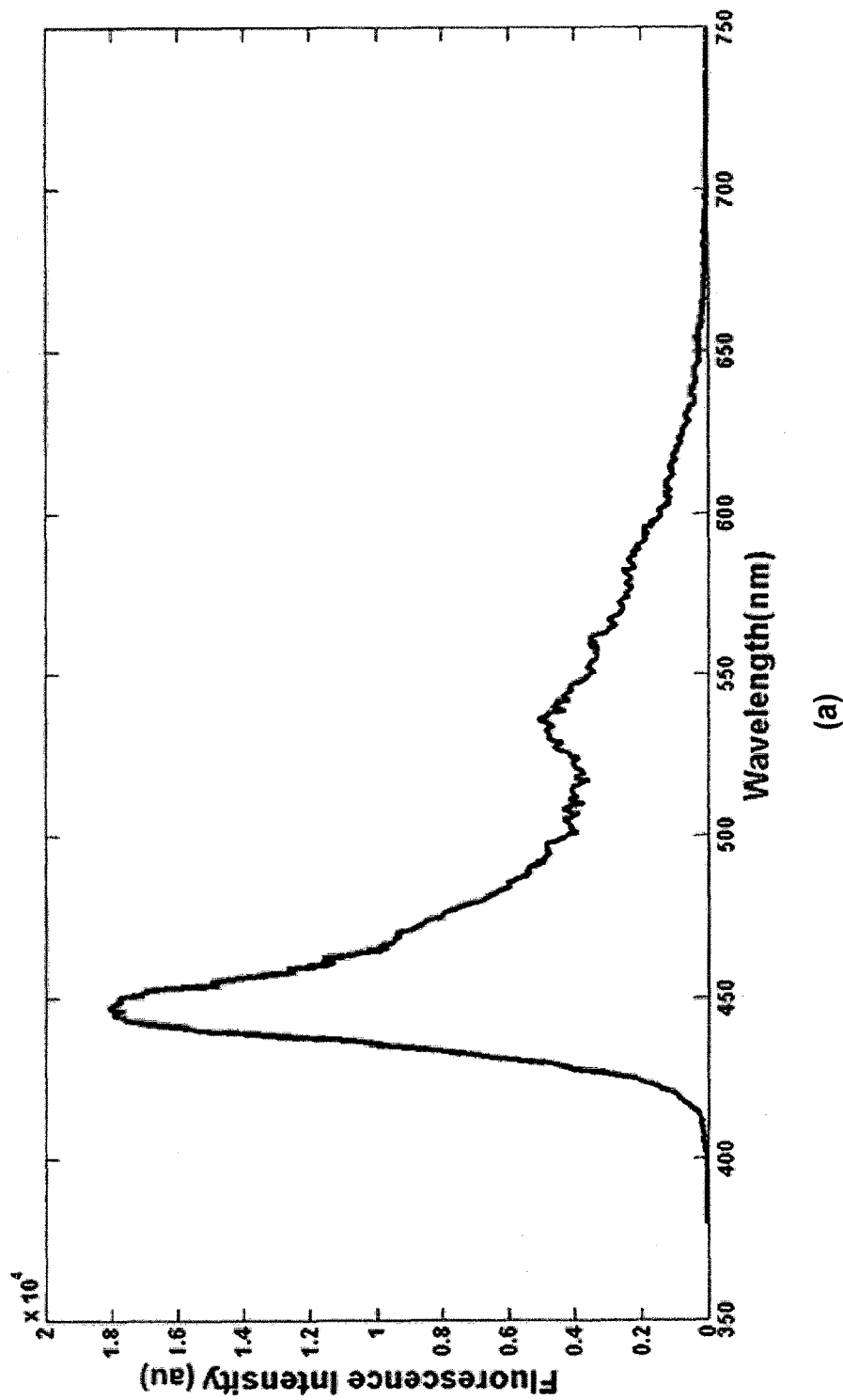
FIGS. 4(a)-4(b) show fluorescence spectra of SWNT-lecithin and SWNT-DPPC interfaces, respectively, in an illustrative embodiment.
Figure 4:
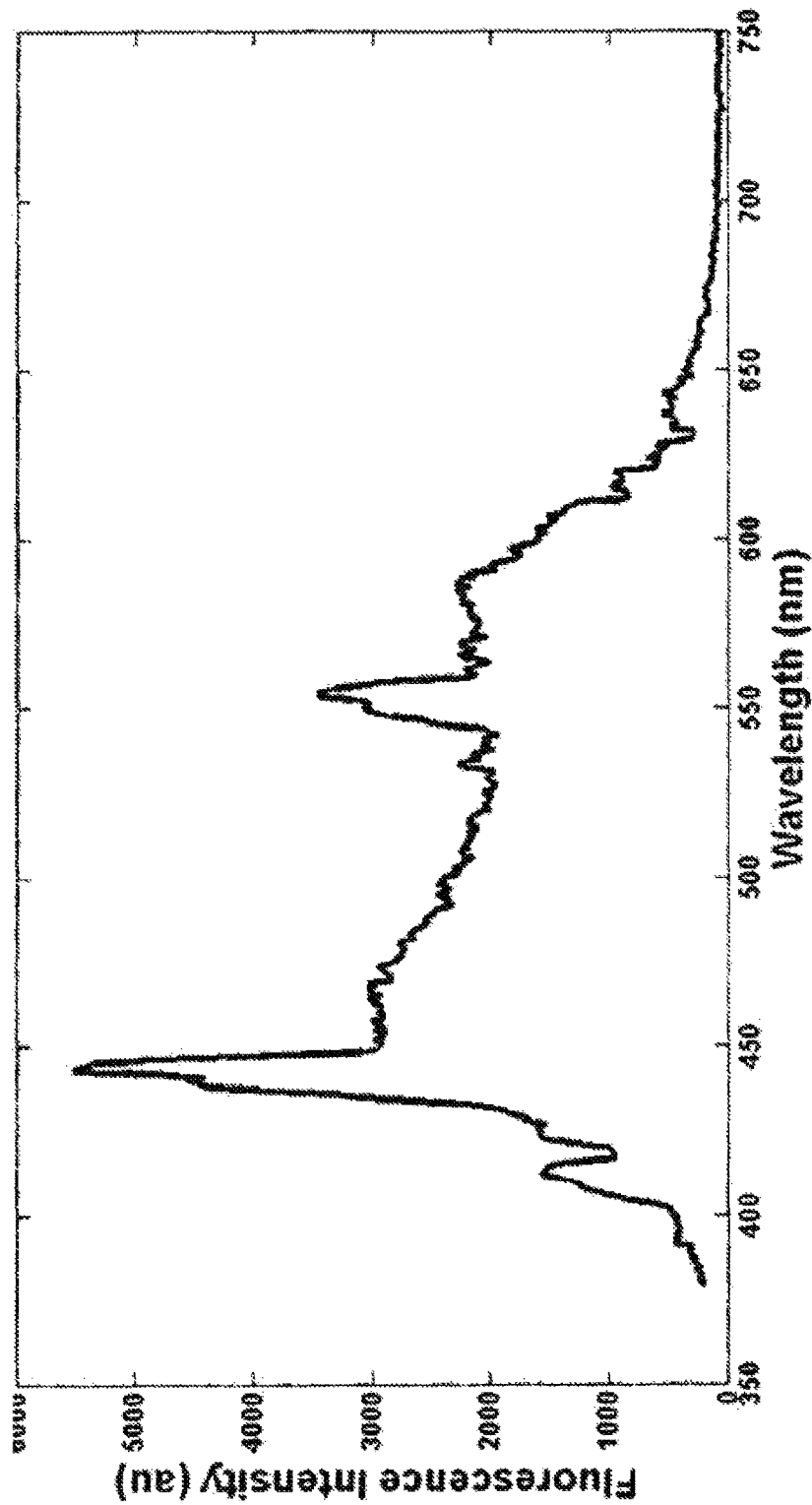
Figure 5:
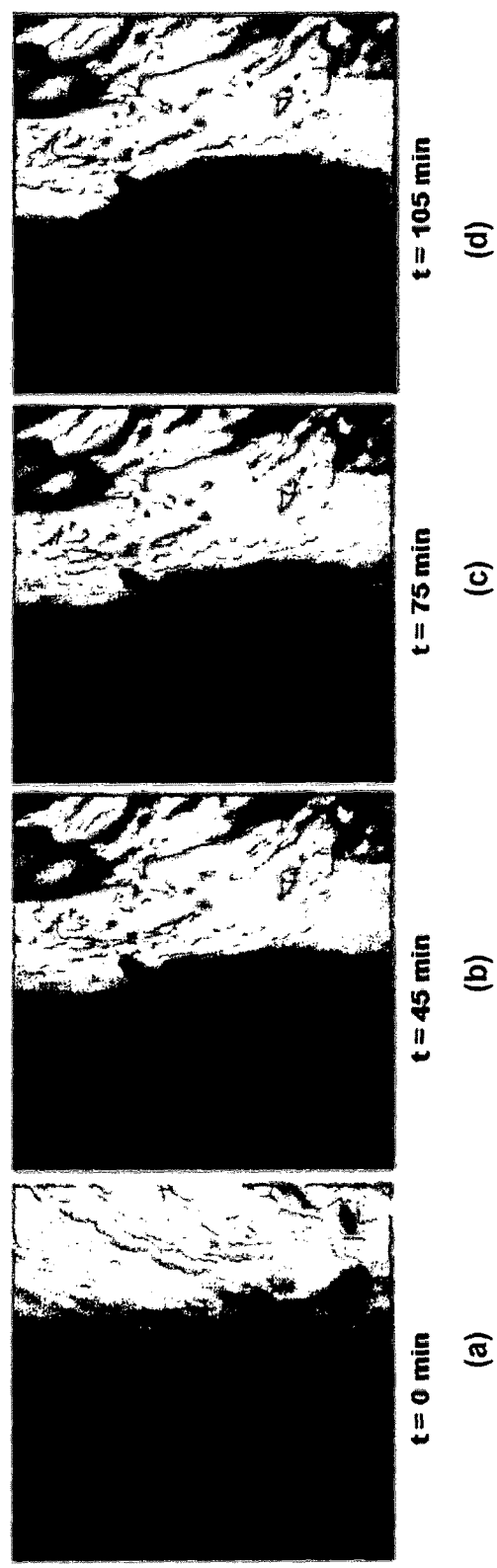
FIGS. 5(a)-5(d) show a series of FT-IR imaging images of SWNT-lecithin interface diffusion at t=0, 45, 105, and 205 minutes, respectively, in an illustrative embodiment.

CNT-Lecithin Interface: The sharp fluorescent layer of SWNT-Lecithin interface was found to shift towards the lipid molecule with time. FIGS. 3(a)-3(c) provide a series of images showing the fluorescent images of the SWNT-lecithin interface at different time intervals (the progression of time is from left to right). Also, FIG. 4(a) and FIG. 4(b) show the fluorescence spectra of SWNT-lecithin and SWNT-DPPC interfaces, respectively. The emission spectra of the interface was observed at about 450 nm when the interface was excited at 360 nm UV radiation. The fluorescence characteristics were found to be similar for MWNT-lecithin interfaces.

CNT-DPPC Interface: DPPC-SWNT fluorescent layer was found to remain fixed at the same position with time. In particular, the diffusion is attenuated for SWNT-DPPC interface. The emission spectra were also observed at about 450 nm when the interface was excited at 360 nm UV radiation, which is similar to SWNT-lecithin interface; the comparison is shown in FIGS. 4(a)-4(b). No such change in spatial translocation of fluorescent SWNT-DPPC interface was observed. The fluorescence characteristics were similar for MWNT-DPPC interfaces.

Because clustering of highly polarizable SWNT was observed, it is postulated that the emission spectra (blue) of the interface correspond to the high band gap energy of the SWNT. If SWNT is highly polarizable and smooth sided, they can form nanorope or bundles with a van der Waals binding energy of about 500 eV per micrometer in tube-tube contact.

As shown in this study, SWNT can form highly ordered nanorope or bundles with the hydrophobic tail of phospholipids in nano-dimension. A highly quantum mechanical confined state can give such sharp fluorescence. As time progressed, SWNT-lipid ordering perturbed the electronic structure of the newly formed nanorope or bundles more, which can affect the band gap energy of SWNT. When this happens, it may perturb the quantum confinement, which results in less quantum yield, which in turn causes a decrease in the fluorescence intensity. Thus the fluorescence study is significant for both the translocation of the SWNT-Lipid interface and also the dependence of fluorescence intensity with the translocation.

FT-IR Imaging:

The phospholipids-CNT interaction at the nano-scale interface was analyzed by an FT-IR Imaging system. It was observed that the extent of drift of the SWNT-Lecithin interface changed significantly with time. However, for DPPC-SWNT, the dynamic was attenuated; the contrast is provided in the series of images provided in FIGS. 5(a)-5(d).

Figure 8:
FIGS. 8(a)-8(b) show FT-IR images of MWNT-lecithin interfaces observed at t=0 and 70 min, respectively, in an illustrative embodiment.
Figure 8:
Figure 9:
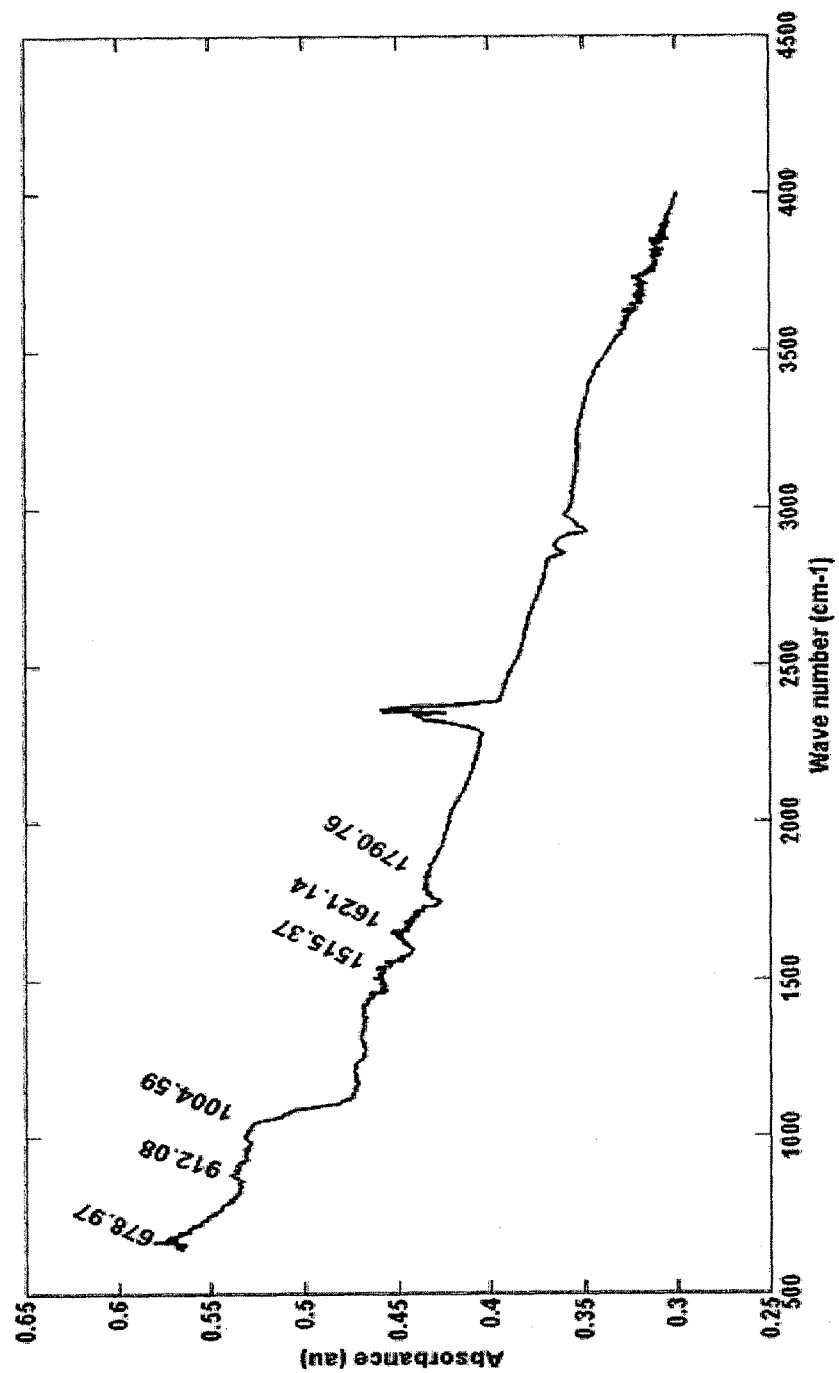
FIGS. 9(a)-9(b) show FT-IR spectra of pristine SWNT and MWNT, respectively, in an illustrative embodiment.
Figure 9:
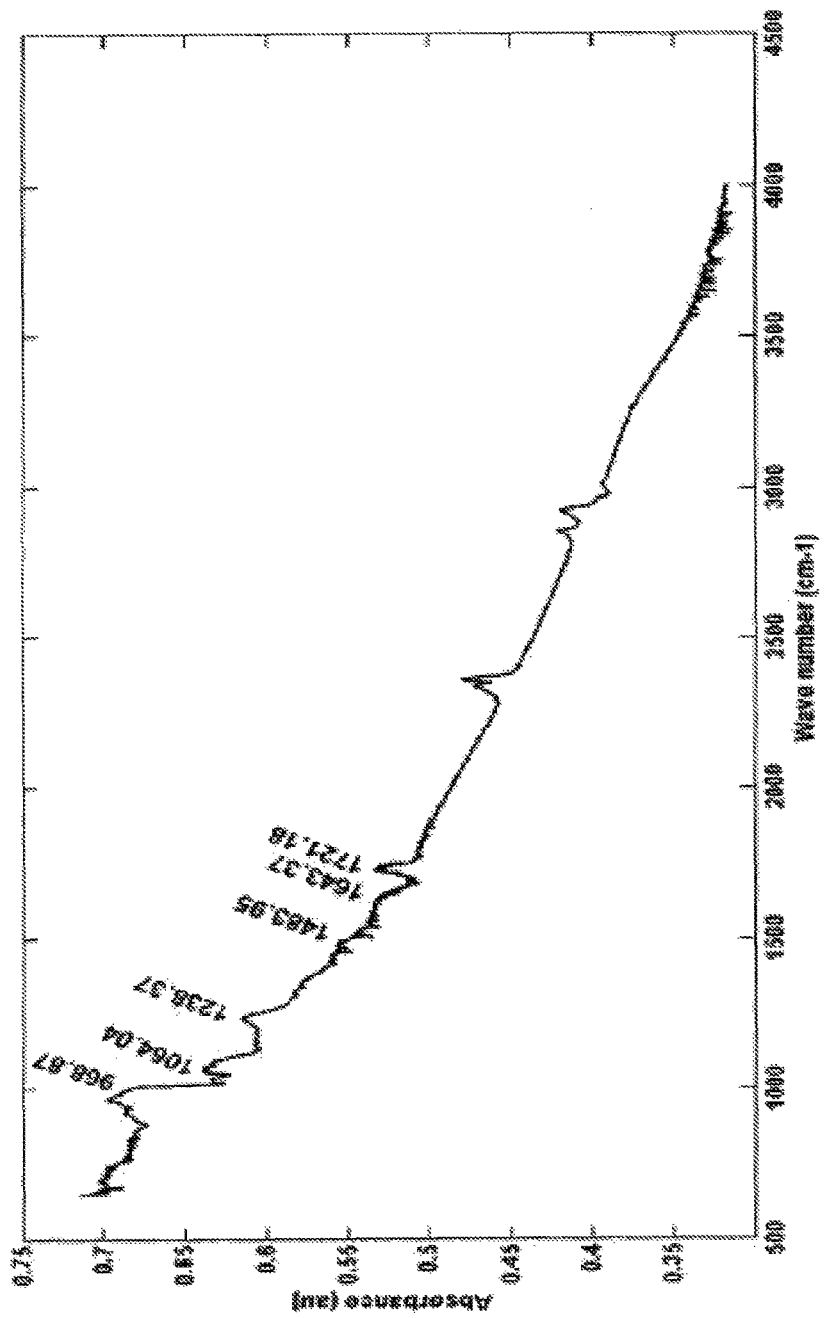

The diffusion of MWNT-Lecithin interface shows faster kinetics for change in the interface meniscus as shown in FIGS. 8(a)-8(b). FIGS. 9(a)-9(b) show the difference in the IR absorbance pattern of pristine SWNT and MWNT respectively.

Solid Diffusion Features:

SWNT-Lecithin Interface Study:

Lecithin has a single linear hydrophobic tail and SWNT is a super-hydrophobic material. With progress of time, the SWNT-Lecithin interface assumes a drift (resembling a parabolic path) towards the lipid molecule. Additionally, an alteration in curvature was observed as shown in FIGS. 6(a)-6(b).

The curvature change was found to be gradual, but there was a central drift after 45 minutes. In accordance with a parabola equation: $(y-y_0)^2=-4a(x-x_0)$, where 'a' is the initial focal length; x and y are variables; and $x_o$ and $y_o$ are the intercepts, when 'a' is infinity then x=constant—i.e. the equation is parallel to the y-axis; or otherwise it can be said that the meniscus is flat, but as 'a' value decreases the radius of curvature gradually increases. Thus the 'a' value is related to the curvature of the SWNT-Lecithin interface meniscus.

MWNT-Lecithin Interface Study:

With progression of time, the MWNT-Lecithin interface was found to also drift towards the lipid molecule, but the drift pattern was not a parabola as observed in the SWNT-Lecithin interface. This is because MWNT is a co-centric cylinder of a number of nanotubes; thus, the hydrophobic tail experiences a hydrophobic pull from each nanotubes, thereby resulting in a fractal pattern in the interface meniscus. Consequently, the extent of such hydrophobic pull was high so that the reaction kinetics was fast, as compared to the SWNT-Lecithin diffusion.

Figure 6:
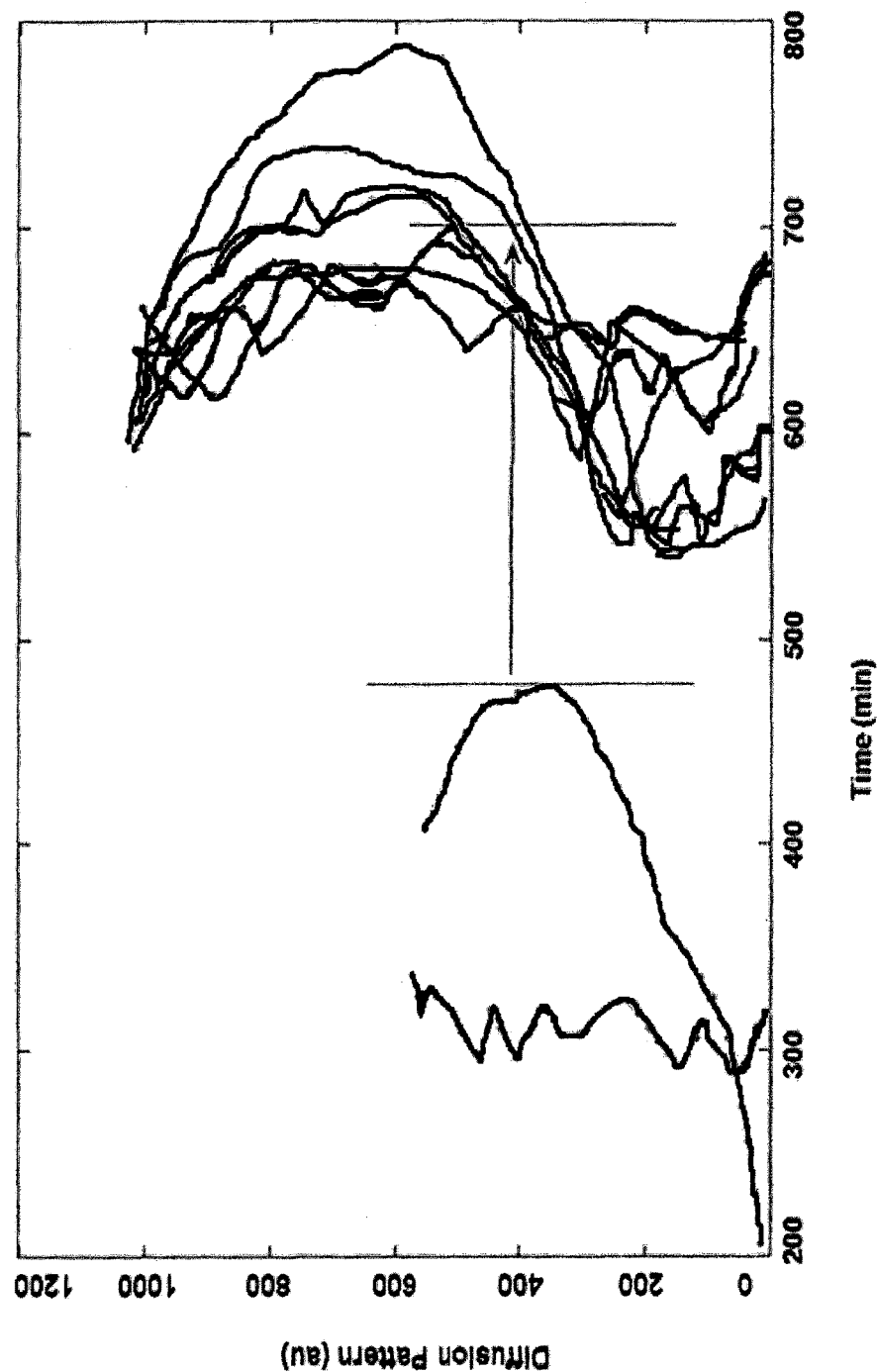
FIGS. 6(a)-6(b) show diffusion pattern of SWNT-lecithin and SWNT-DPPC interfaces, respectively, with time in an illustrative embodiment.
Figure 6:
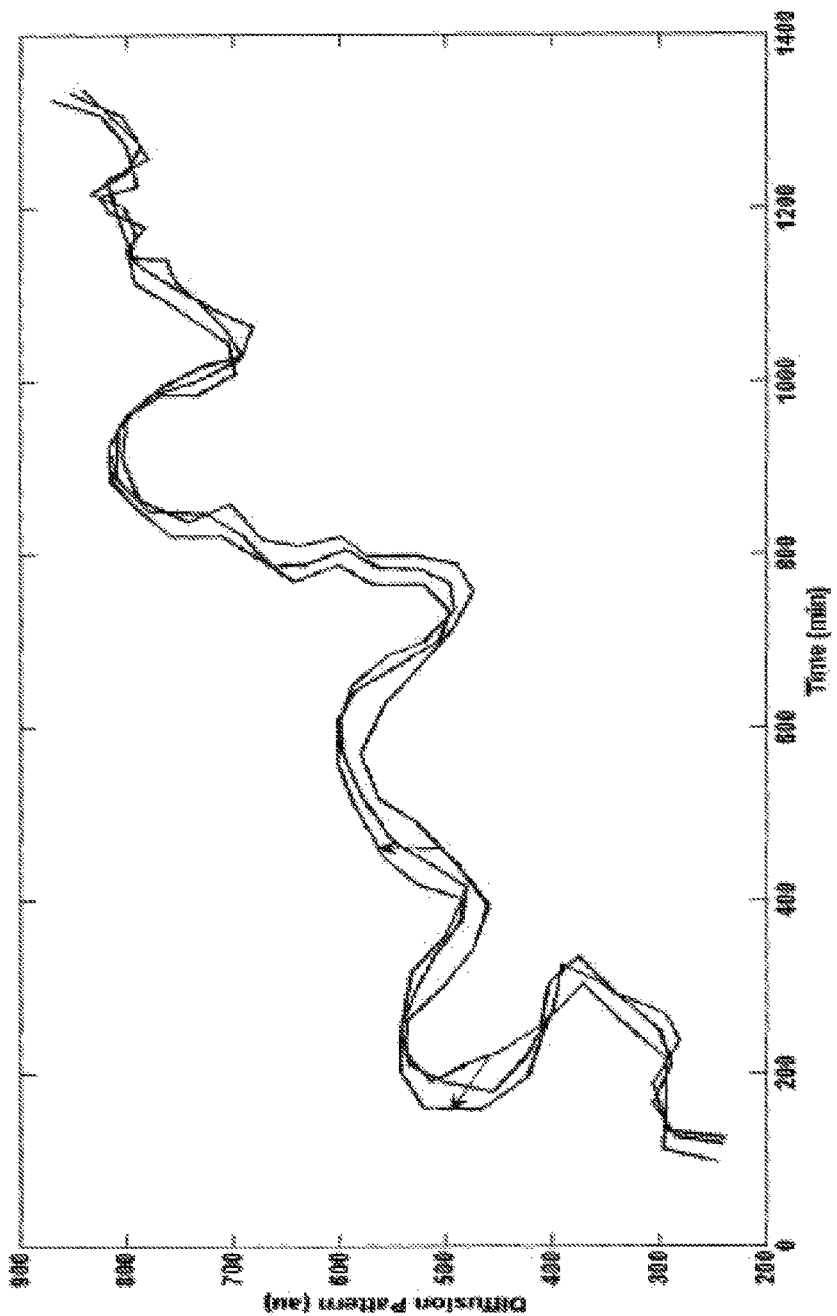

SWNT-DPPC Interface Study:

DPPC is a modified lecithin with two palmitic acid chains in C1 and C2 carbon position. The reaction kinetics was found attenuated and the diffusion pattern was found highly non-planar for SWNT-DPPC Interface as shown in FIG. 6.

As the interface geometry was found to be non-Euclidian, no mathematical formulation was developed for such a fractal interface.

The reaction was also found to be attenuated and the diffusion pattern was also found to be highly non-planar for MWNT-DPPC interface, which was similar to the SWNT-DPPC interface.

Comparative Study of Two CNT-Lipid Interfaces:

The interface geometry, diffusion rate, and the extent of diffusion were found to be different for the two CNTs and different lipids observed in this study.

For CNT part, it may be due to the fact that MWNT was a co-centric cylinder of a number of nanotubes such that the hydrophobic tail of lipid experienced hydrophobic pull from each nanotubes, thereby resulting in a fractal pattern in the interface meniscus. As a result, there was a drift of the interface towards the lipid molecule.

On the other hand, for the lipid part it may be due to the fact that lecithin, which is a single tail phospholipids, differs structurally from DPPC, which is a branched phospholipids. As DPPC has two hydrophobic tails with same level of hydrophobicity, SWNT experience the same extent of hydrophobic push from the two tails of the phospholipids. Thus, the solid state diffusion pattern depends on the molecular complexity of the interacting molecules. In other words, this study shows that the different lipids (with respect to linear or branched hydrophobic tails or even different levels of hydrophobicity) may be distinguished based on their interactions with the CNT probes.

It was shown that SWNT, MWNT, and lipid molecules interact with one another when exposed to one another in the solid phase. The interaction was observed from the dynamics of the interface movements, more precisely the SWNT/MWNT approaches towards the lipid molecule. The extent of this diffusion is dependent on the structure of both of the CNT type and lipid type. MWNT showed a faster diffusion rate but a fractal pattern compared to SWNT. On the other hand, branch-chain lipids exhibited slower diffusion, compared to single chain, linear, lipids. The interface movements allow lipid profiling based on molecular structure as well as on electronic properties and chiralities of the CNTs.

Further, the foregoing shows that in the presence of an amphiphilic molecule, the hydrophobic side of the molecule will orient towards the CNT.

Raman Spectroscopy for Different Nanotubes

Figure 10:
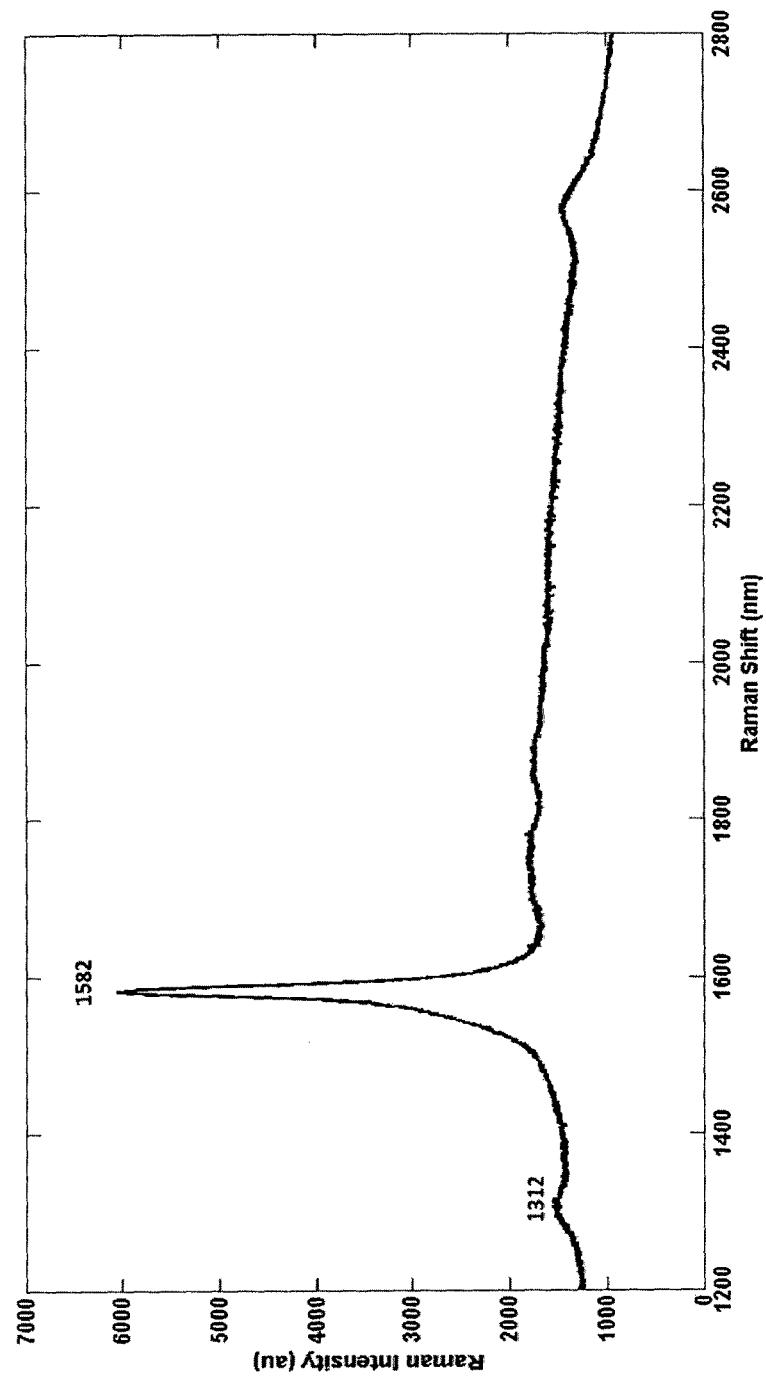
FIG. 10 shows Raman spectra of pristine single wall carbon nanotubes.
Figure 11:
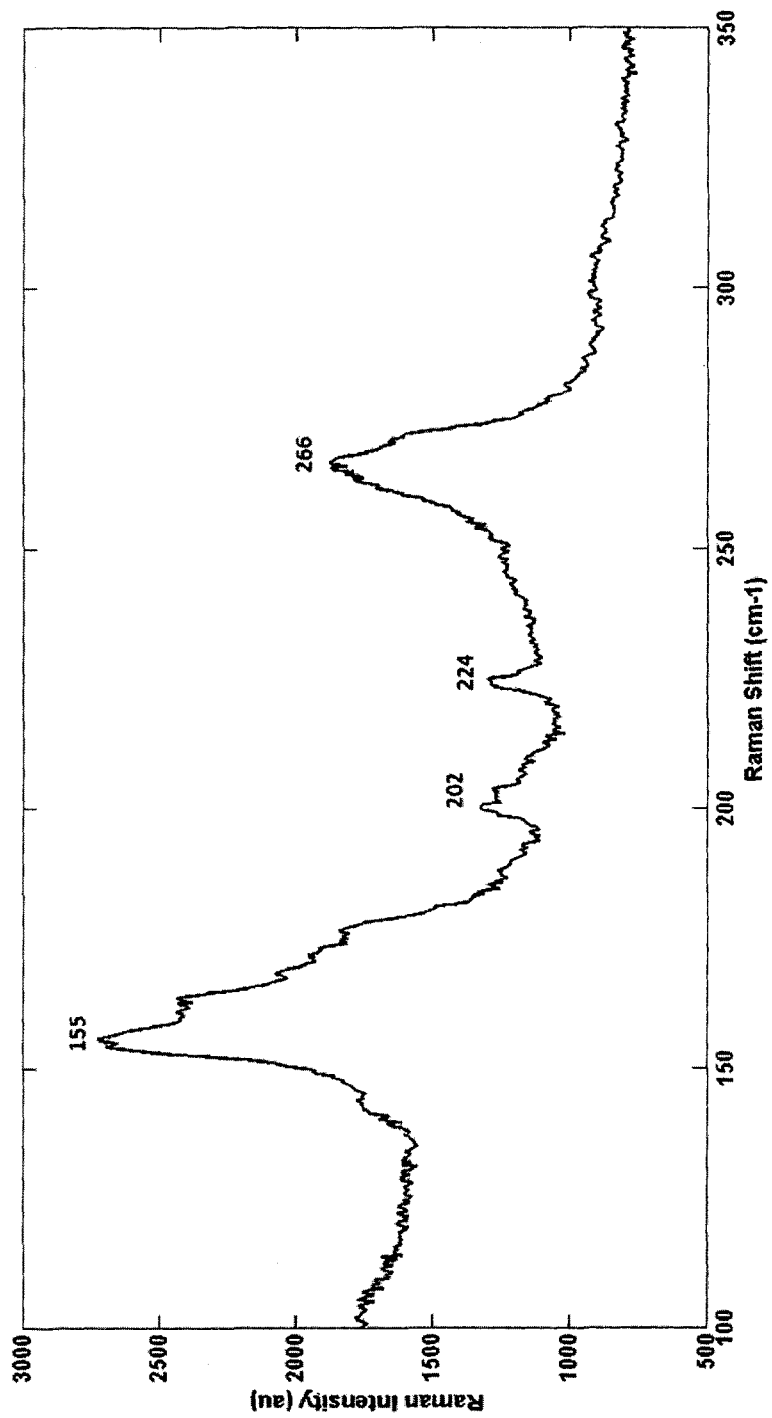
FIG. 11 shows Radial breathing modes (RBM) of Raman spectroscopy of pristine single wall carbon nanotubes.
Figure 12:
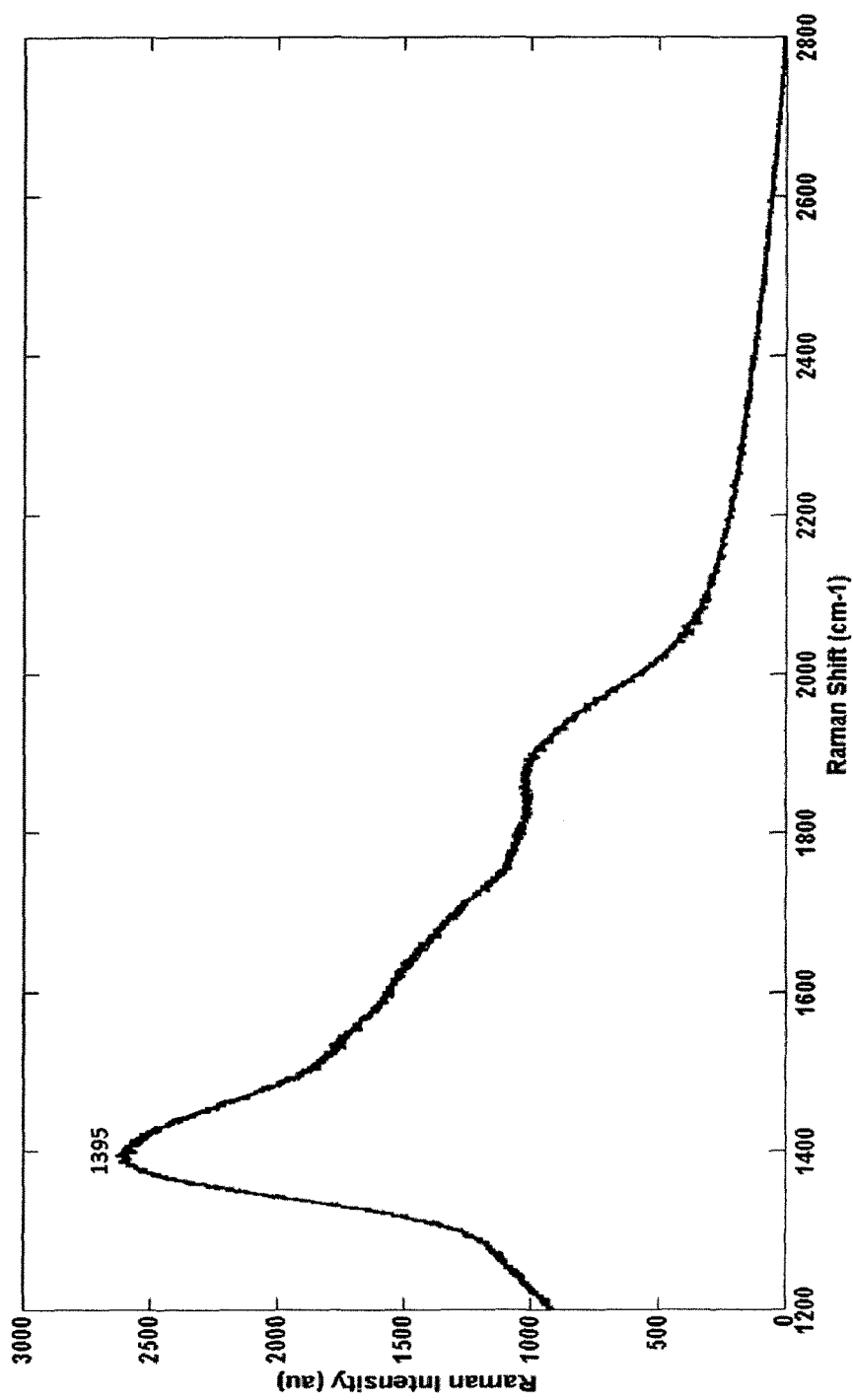
FIG. 12 shows Raman spectra of single wall carbon nanotubes functionalized with lecithin.
Figure 13:
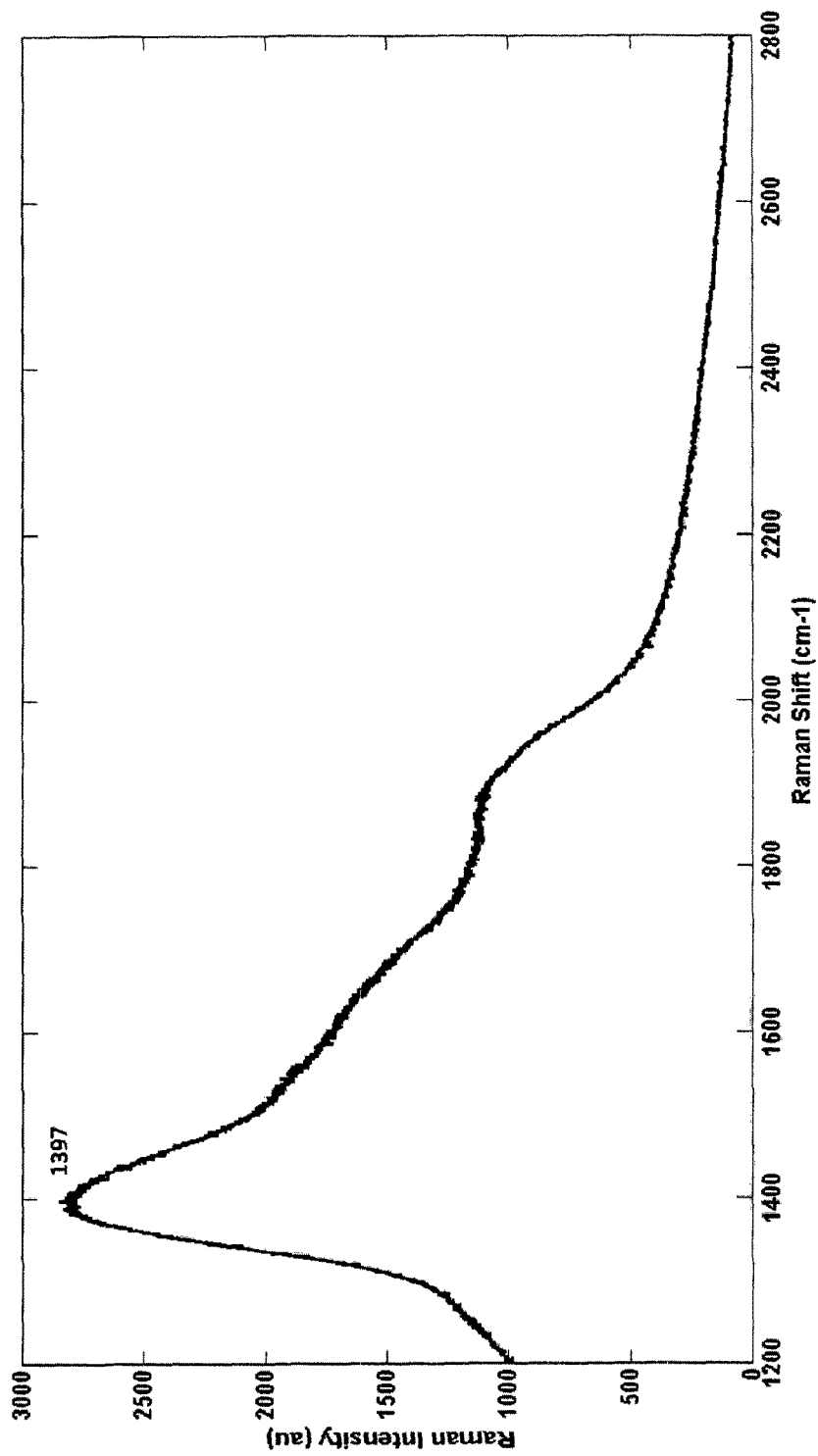
FIG. 13 shows Raman spectra of single wall carbon nanotubes functionalized with Dipalmitoyl Phosphatidylcholine.
Figure 14:
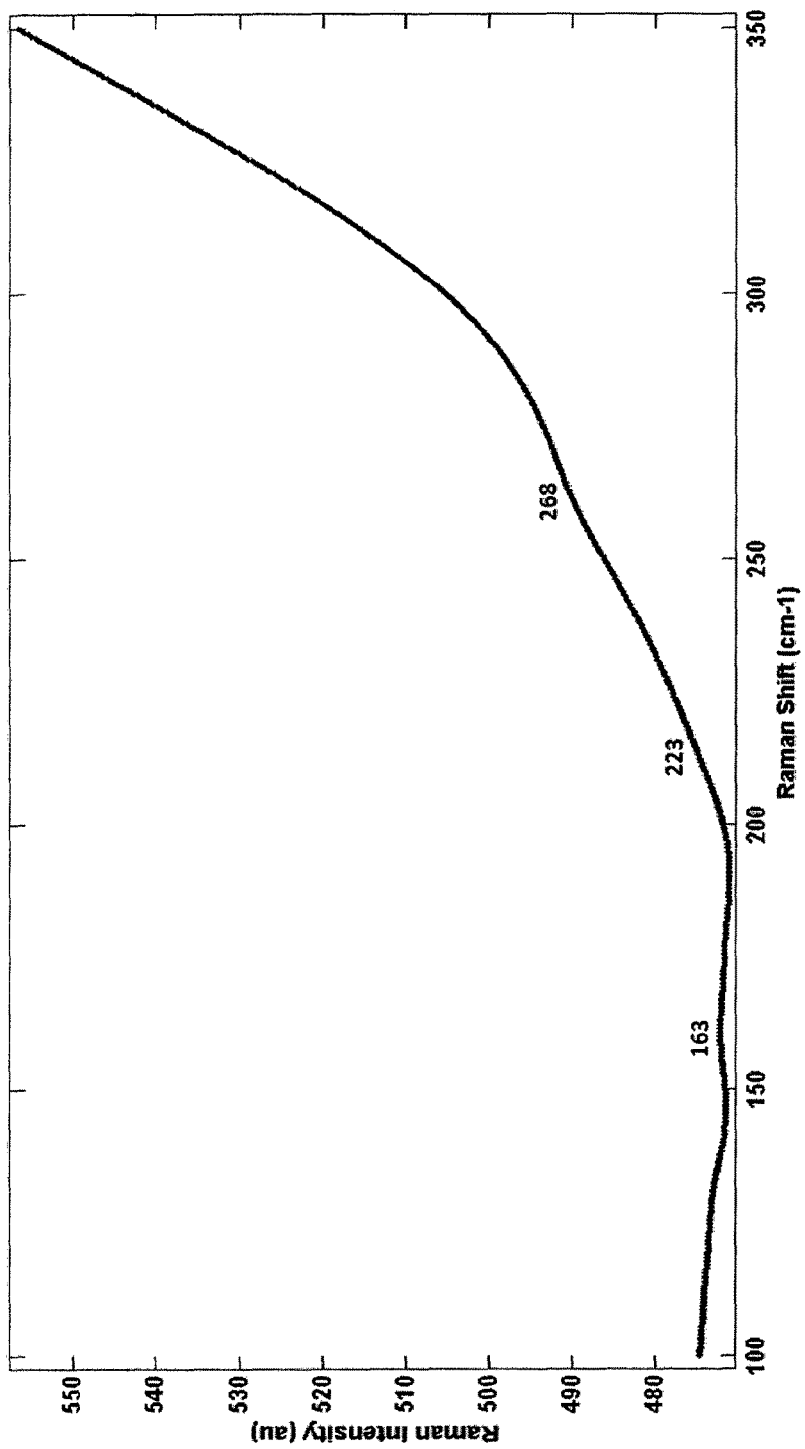
FIG. 14 shows radial breathing modes (RBM) of lecithin functionalized single wall carbon nanotubes.
Figure 15:
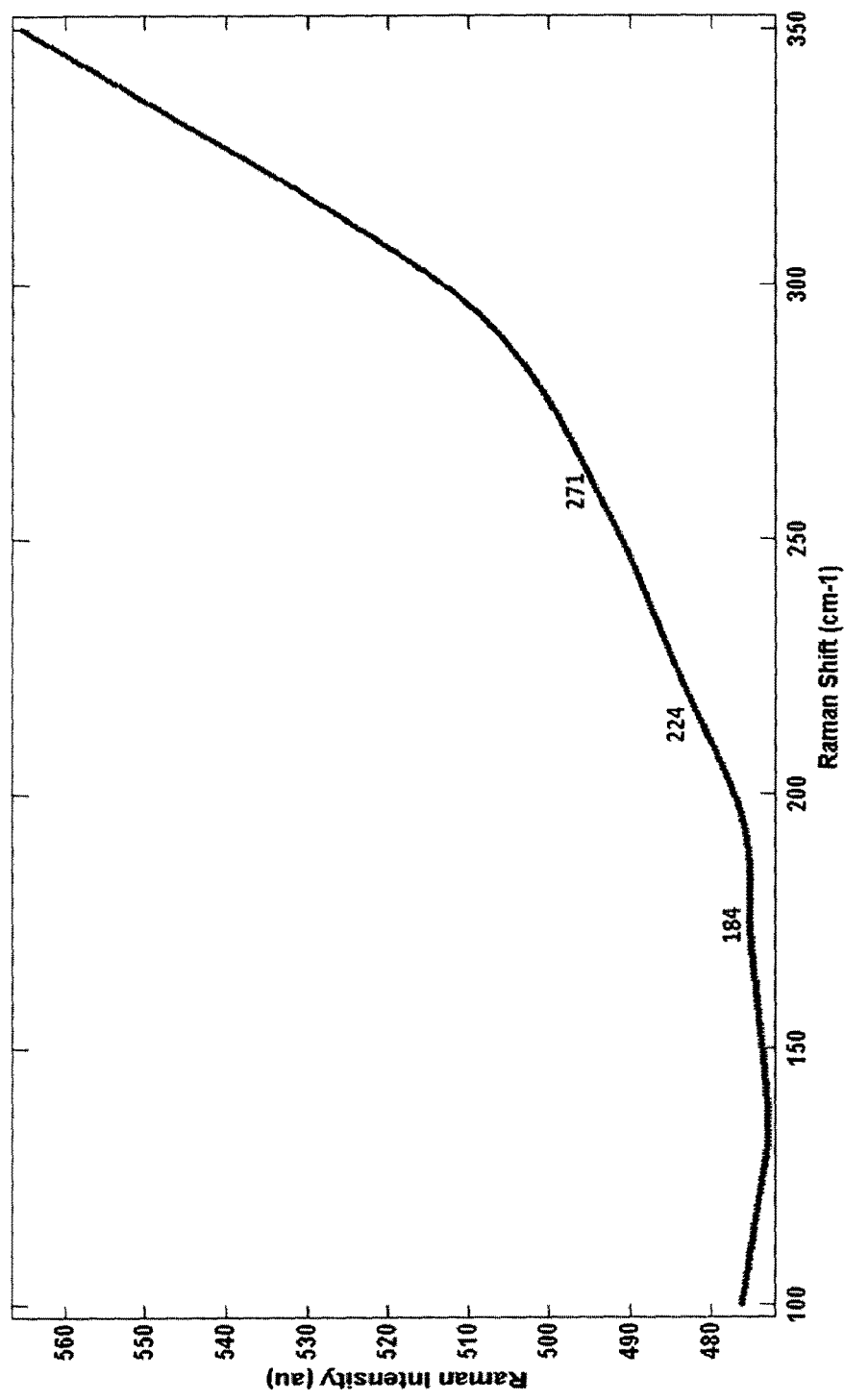
FIG. 15 shows radial breathing modes (RBM) of DPPC functionalized single wall carbon nanotubes.

Raman spectra were obtained using a confocal Micro Raman spectrometer (LabRAM HR Vis. Horiba Jobin Yvon SAS France). The results were shown in FIGS. 10-15. Specifically, FIGS. 10 and 11 show Raman spectra and the spectra in the radial breathing modes (RBM), respectively, of pristine single wall carbon nanotubes. FIGS. 12 and 13 show Raman spectra of single wall carbon nanotubes functionalized with lecithin and Dipalmitoyl Phosphatidylcholine, respectively. FIGS. 14 and 15 show RBM of lecithin functionalized single wall carbon nanotubes and DPPC functionalized single wall carbon nanotubes, respectively.

It was observed that for the excitation wavelength 785 nm, grating 1200 g/mm, 50×NIR objective having numerical aperture 0.55 giving the best confocality—i.e., at the depth of focus~2 μm, there was no loss of Raman signal with the confocal size 100±5 μm. As shown in FIGS. 10-15 because the maximum diameter of the illuminated spot on the sample was ~1 μm, there was minimal loss of Raman signal from the pristine/functionalized SWNT sample under the operating conditions of the spectrometer as described above. Also, the SWNT functionalization by lipids was verified via the RAMAN spectroscopy, as shown in FIGS. 12 and 13.

EQUIVALENTS

The embodiments, illustratively described herein may suitably be practiced in the absence of any element or elements, limitation or limitations, not specifically disclosed herein. Thus, for example, the terms 'comprising,' 'including,' 'containing,' etc., shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase 'consisting essentially of' will be understood to include those elements specifically recited and those additional elements that do not materially affect the basic and novel characteristics of the claimed technology. The phrase 'consisting of' excludes any element not specified.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent compositions, apparatuses, and methods within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

The present technology has thus been described broadly and generically. Each of the narrower species and subgeneric groupings falling within the generic disclosure also forms part of the technology. This includes the generic description of the technology with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, particularly in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as 'up to,' at least, 'greater than,' 'less than,' and the like, include the number recited and refer to ranges which can be subsequently broken down into subranges as discussed above. Finally, as will be understood by one skilled in the art, a range includes each individual member.

While certain embodiments have been illustrated and described, it should be understood that changes and modifications can be made therein in accordance with ordinary skill in the art without departing from the technology in its broader aspects as defined in the following claims.

We claim:

1. A method comprising:
   contacting, in the solid state, a sample comprising a first organic molecule with a composition comprising a carbon nanotube, such that an interface forms between the sample and the composition;
   observing any movement of the interface; and
   characterizing the first organic molecule based on the observed movement.

2. The method of claim 1, wherein the first organic molecule is a lipid.

3. The method of claim 2, wherein the lipid comprises a linear hydrophobic group.

4. The method of claim 2, wherein the lipid comprises a branched hydrophobic group.

5. The method of claim 1, wherein the first organic molecule is a phospholipid, glycolipid, sphingolipid, steroid, or a combination of any two or more thereof.

6. The method of claim 1, wherein the carbon nanotube is a single wall carbon nanotube.

7. The method of claim 1, wherein the carbon nanotube is a multiwall carbon nanotube.

8. The method of claim 1, wherein the carbon nanotube is not chemically functionalized prior to contact with the sample.

9. The method of claim 1, wherein the contacting comprises contacting the sample with the composition at room temperature.

10. The method of claim 1, wherein the contacting comprises contacting the sample with the composition at about 1 atmosphere pressure.

11. The method of claim 1, wherein observing any movement comprises observing the movement of the interface via optical microscopy, fluorescence microscopy, Raman microscopy, infra-red imaging, thermal imaging, or a combination of any two or more thereof.

12. The method of claim 1, wherein observing any movement comprises observing the rate of the movement of the interface.

13. The method of claim 1, wherein observing any movement of the interface comprises observing the composition moving towards the first organic molecule.

14. The method of claim 1, further comprising:
   contacting, in the solid state, a second sample comprising a second organic molecule with a composition comprising a carbon nanotube, such that a second interface forms between the second sample and the composition;
   observing any movement of the second interface; and
   distinguishing the second organic molecule from the first organic molecule based on observations of the movements associated with the respective interfaces.

15. A method comprising:
   contacting, in the solid state, a sample comprising at least one of (i) an amphiphilic organic molecule and (ii) a non-amphiphilic organic molecule with a composition comprising a carbon nanotube, such that an interface forms between the sample and the composition;
   observing any movement of the interface; and
   characterizing at least one of the amphiphilic organic molecule and the non-amphiphilic organic molecule based on the observed movement.

16. The method of claim 15, wherein observing any movement comprises observing diffusion of at least one of (i) the amphiphilic or non-amphiphilic organic molecule and (ii) the composition.

17. The method of claim 15, wherein the amphiphilic or non-amphiphilic organic molecule is lecithin, dipalmitoyl phosphatidylcholine (DPPC), sphingomyelins, or sphingosine.

18. The method of claim 15, wherein observing any movement of the interface comprises observing by fluorescence spectroscopy.

19. The method of claim 18, wherein the observing by fluorescence spectroscopy comprises observing the interface by fluorescence spectroscopy wherein the amphiphilic or non-amphiphilic organic molecule and the composition not at the interface are substantially free of fluorescence.

20. The method of claim 15, wherein the interface exhibits quantum confinement.

21. The method of claim 15, wherein the carbon nanotube has a diameter of about 2 to about 3 nm.

* * * * *